(12) United States Patent
Burek et al.

(10) Patent No.: US 6,573,367 B1
(45) Date of Patent: Jun. 3, 2003

(54) DERIVATIVES FROM THE CLASS OF OLEANDOMYCIN

(75) Inventors: Gordana Burek, Zagreb (HR); Gorjana Lazarevski, Zagreb (HR); Gabrijela Kobrehel, Zagreb (HR)

(73) Assignee: Pliva, farmaceutska industrija, dionicko drustvo, Zagreb (HR)

( * ) Notice: Subject to any disclaimer, the term of this patent is extended or adjusted under 35 U.S.C. 154(b) by 0 days.

(21) Appl. No.: 09/869,606

(22) PCT Filed: Dec. 29, 1999

(86) PCT No.: PCT/HR99/00035

§ 371 (c)(1), (2), (4) Date: Jul. 2, 2001

(87) PCT Pub. No.: WO00/40589

PCT Pub. Date: Jul. 13, 2000

(30) Foreign Application Priority Data

Dec. 30, 1998 (HR) ............................. P980646A

(51) Int. Cl.⁷ ............... C07H 1/00; C07H 17/08
(52) U.S. Cl. ............ 536/7.2; 536/7.1; 536/4.1; 536/124; 514/28; 514/29; 514/25; 514/34
(58) Field of Search .................. 536/7.2, 7.1, 4.1, 536/124; 514/28, 29, 25, 34

(56) References Cited

U.S. PATENT DOCUMENTS 5,004,734 A * 4/1991 Philippe et al. .............. 514/29
5,250,518 A * 10/1993 Kobrehel et al. ............. 514/29

(List continued on next page.)

OTHER PUBLICATIONS

Nagel et al. " Macrolide neutral sugar chemistry. Chemical conversion of oleandomycin Y to 3–(2,6–dideoxy–L–alpha–allosyl) oleandomycin Y and 3–(2,6–dideoxy–L–alpha–galactosyl)oleandomycin Y." J. org. Chem. (1982), 47(24), 4796–99.*

Paterson, "Studies in macrolide synthesis: a synthesis of two chiral fragments of oleandomycin and lankamycin." Tetrahedron Lett. (1983), 24(12), 1311–14.*

* cited by examiner

Primary Examiner—Samuel Barts
Assistant Examiner—Devesh Khare
(74) Attorney, Agent, or Firm—Connolly Bove Lodge & Hutz, LLP

(57) ABSTRACT

The invention relates to novel compounds from the class of the macrolide antibiotic oleandomycin of the general formula (I)

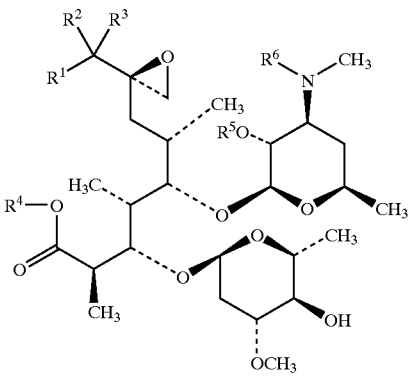

wherein $R^1$ has the individual meaning of —$CH_2CH_3$ group, of a fragment of the formula (II), together with $R^2$ has the meaning of a fragment of the formula (III) or together with $R^4$ has the meaning of a fragment of the formula (IV) or a fragment of the formula (V)

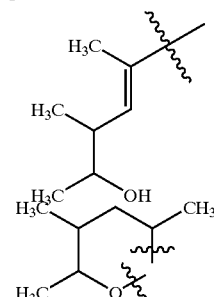

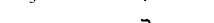

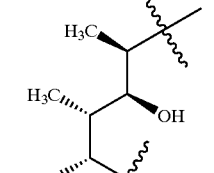

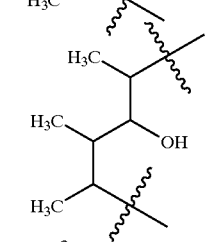

$R^2$ together with $R^3$ has the meaning of a ketone or together with $R^1$ has the meaning of a fragment of the formula (III), $R^3$ has the individual meaning of OH group or together with $R^2$ has the meaning of a ketone, $R^4$ has the individual meaning of a methyl group, or together with $R^1$ has the meaning of a fragment of the formula (IV) or of a fragment of the formula (V), $R^5$ has the individual meaning of hydrogen or a benzyloxycarbonyl group, $R^6$ has the individual meaning of hydrogen, a methyl group or a benzyloxycarbonyl group, to intermediates for the preparation thereof, to a process for preparing them as well as to pharmaceutically acceptable addition salts thereof with inorganic or organic acids.

24 Claims, No Drawings

DERIVATIVES FROM THE CLASS OF OLEANDOMYCIN

TECHNICAL FIELD

1. Technical Problem

The invention relates to novel compounds from the class of the macrolide antibiotic oleandomycin, to intermediates for the preparation thereof, to a process for preparing them as well as to pharmaceutically acceptable addition salts thereof with inorganic or organic acids.

2. Prior Art

Oleandomycin is a macrolide antibiotic (U.S. Pat. No. 2,757,123) having an activity spectrum similar to that of erythromycin A. The oleandomycin structure is characterized by a 14-member lactone ring with a keto group in C-9 position, by the sugar desosamin in C-5 position and by the sugar oleandrose in C-3 position as well as by three OH groups. It differs from other polyoxo macrolides by an exocyclic epoxide ring on C-8 atom. Earlier investigations (JACS 82, 3225–3227, 1960; JOC 51, 5397–5400, 1986) showed its exceptional sensitivity both in acidic and basic conditions. In an acidic medium C-8 epoxide is opened, oleandrose is cleaved and a contraction of the aglycone ring takes place. The action of a base causes a dehydratation of H-10 and OH-11 under the generation of C-10/C-11 double bond to give anhydrooleandomycin. All these transformations cause a loss of the antibiotic action.

It is known that similar transformations at erymromycin A with OH groups participating are successfully inhibited by O-methylation thereof (Watanabe Y. and al, U.S. Pat. No. 4,331,803, 5/1982). By the reaction of erymromycin A with benzyloxycarbonyl chloride and then by methylation of the obtained 2'-O,3'-N-bis(benzyloxycarbonyl)-derivatives, after elimination of protecting groups and N-methylation, there are obtained, in addition to 6-O-methyl erythromycin (CLARITHROMYCIN), significant amounts of 11-O-methyl erythromycin and polysubstituted analogues (Morimo S. et al, J. Antibiotics 1984, 37, 187). Clarithromycin is significantly more stable in an acidic medium than erythromycin A and shows enhanced in vitro activity against Gram positive bacterial strains (Kirst H. A. et al. Antimicrobial Agents and Chemother., 1989, 1419). Similarly, also a series of O-methyl derivatives of azythromycin was synthesised (Kobrehel G. et al, U.S. Pat. No. 5,250,518, 5/1993).

Our efforts to inhibit the formation of an inactive anhydrooleandomycin by O-methylation of C-11 hydroxyl group, retroaldol fragmentation, dehydratation and isomerisation took place and led to a series of linear and cyclic derivatives of oleandomycin, not yet disclosed so far, which may serve as intermediates for chimeric oleandomycins with potential biological action.

The synthesis of these derivatives involves a reaction of oleandomycin with benzyloxycarbonyl chloride to obtain 2'-O,3'-N-bis(benzyloxycarbonyl)-3'-N-demethyl oleandomycin, a reaction with methyl iodide in the presence of sodium hydride, an elimination of protecting groups on 2' and 3' positions and reductive 3'-N-methylation.

Oleandomycin derivatives according to the present invention and their pharmaceutically acceptable addition salts with inorganic or organic acids, methods and intermediates for the preparation thereof have not been disclosed in Prior Art.

DESCRIPTION OF THE INVENTION WITH EXAMPLES

Novel derivatives of oleandomycin of the general formula (I)

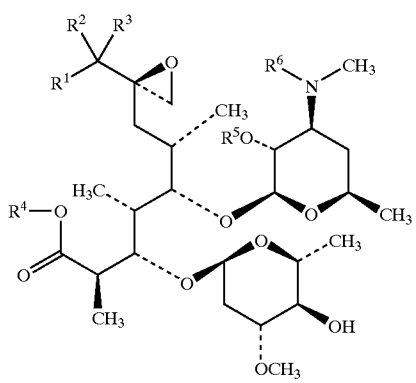

wherein

R$^1$ has the individual meaning of —CH$_2$CH$_3$ group, of a fragment of the formula (II), together with R$^2$ has the meaning of a fragment of the formula (III) or together with R$^4$ has the meaning of a fragment of the formula (IV) or a fragment of the formula (V)

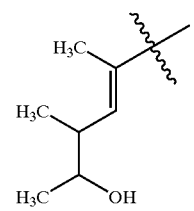

II

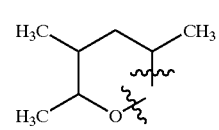

III

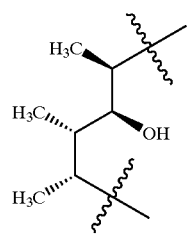

IV

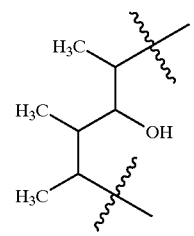

V

R² together with R³ has the meaning of a ketone or together with R¹ has the meaning of a fragment of the formula (III), R³ has the individual meaning of OH group or together with R² has the meaning of a ketone, R⁴ has the individual meaning of a methyl group, or together with R¹ has the meaning of a fragment of the formula (IV) or of a fragment of the formula (V), R⁵ has the individual meaning of hydrogen or a benzyloxycarbonyl group, R⁶ has the individual meaning of hydrogen, a methyl group or a benzyloxycarbonyl group, and their pharmaceutically acceptable addition salts with inorganic or organic acids, are obtained as follows.

Fragment IV is one of one of sixteen diasteroisomers of fragment V. As is known to persons of skill in the chemical arts, a wedge-shaped bond represents bonding to a group projecting above the plane of the paper. As is known to persons of skill in the chemical arts, a stippled bond represents bonding to a group projecting below the plane of the paper. For purposes of lexicography, we individually name the sixteen diastereoisomers of Fragment V with respect to the projection of the various bonds starting with the bond closest to the top of the page, With reference to fragment IV, the bond to methyl nearest the top of the page, projects up (U), the bond to hydroxyl projects up (U), continuing down the page, the bond to methyl projects down (D), and the bond to methyl towards the bottom of the page projects down (D). Thus we name Fragment IV, the UUDD diastereoisomer of Fragment V, Fragment VI. Retaining the same naming convention, there are four UU diastereoisomers (UUDD, V1; UUUD, V2; UUDU, V3; UUUU, V4). There are four DD diastereoisomers (DDDD, V5; DDUD, V6; DDDU, V7; DDUU, V8). There are four DU diastereoisomers (DUDD, V9; DUUD, V10; DUDU, V11; DUUU, V12). There are four UD diastereoisomers (UDDD, V13; UDUD, V14; UDDU, V15; UDUU, V16)

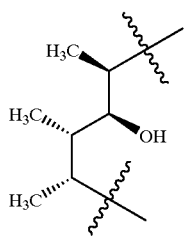

IV

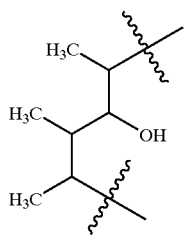

V

Step 1:

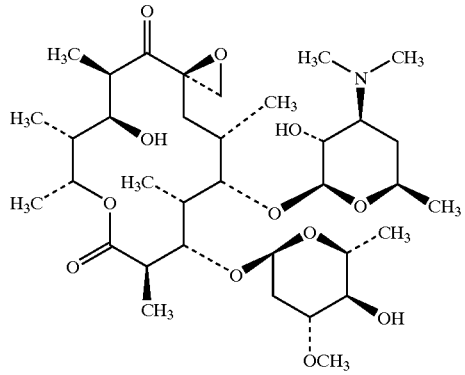

VI

By subjecting oleandomycin of the formula (VI) to a reaction with benzyloxycarbonyl chloride in the presence of bases, preferably sodium hydrogen carbonate, in a solvent inert in the reaction, preferably benzene or toluene, there is obtained 2'-O,3'-N-bis(benzyloxycarbonyl)-3'-N-demethyl-oleandomycin of the general formula (I), wherein R¹ together with R⁴ has the meaning of a fragment of the formula (IV), R² together with R³ has the meaning of a ketone and R⁵ and R⁶ are the same and have the meaning of a benzyloxycarbonyl group.

Step 2:

By a reaction of 2'-O,3'-N-bis(benzyloxycarbonyl)-3'-N-demethyl-oleandomycin from Step 1 with 1.3–3.25 equivalents of the corresponding methylation agent, preferably methyl iodide, and 1.1–3.75 equivalents of the corresponding base, preferably sodium hydride, at a temperature from −15° C. to room temperature, preferably at 0–5° C., in an appropriate aprotic solvent or solvent mixture, preferably DMSO-THF=1:1, and by separation on a silica gel column in the system toluene-ethyl acetate=1:1 there is obtained a compound 2A of the general formula (I), wherein R¹ has the individual meaning of —CH₂CH₃ group, R² together with R³ has the meaning of a ketone, R⁴ is a methyl group and R⁵ and R⁶ are the same and have the meaning of a benzyloxycarbonyl group, a compound 2B of the general formula (I), wherein R¹ together with R⁴ has the meaning of a fragment of the formula (V), R² together with R³ has the meaning of a ketone and R⁵ and R⁶ are the same and have the meaning of a benzyloxycarbonyl group, and a compound 2C of the general formula (I), wherein R¹ has the individual meaning of a fragment of the formula (II), R² together with R³ has the meaning of a ketone, R⁴ is a methyl group and R⁵ and R⁶ are the same and have the meaning of a benzyloxycarbonyl group.

The relative ratio of chromatographically homogenous products depends upon the equimolar ratio of reactants.

Step 3:

Each of the oleandomycin derivatives from Step 2 is separately subjected to a hydrogenolysis reaction in order to eliminate protecting benzyloxycarbonyl groups in 2' and 3' positions according to the method by E. H. Flynn et al (Journal of American Chemical Society, 77, 3104, 1950). Hydrogenolysis is carried out in a lower alcohol solution, preferably in ethanol, in the presence of NaOAc/HOAc buffer (pH 5), with a catalyst such as palladium black or palladium on carbon, under hydrogen pressure of 10⁵ Pa at room temperature to obtain, respectively, in case of 2A, a compound 3A of the general formula (I), wherein $R^1$–$R^4$ have the meanings as given for the compound 2A and $R^5$ and $R^6$ are the same and have the meaning of hydrogen, and in case of 2B, a compound 3B of the general formula (I), wherein $R^1$–$R^4$ have the meanings as given for the compound 2B and $R^5$ and $R^6$ are the same and have the meaning of hydrogen, and in case of 2C, a compound 3C of the general formula (I), wherein $R^1$ together with $R^2$ has the meaning of a fragment of the formula (III), $R^3$ is an OH group, $R^4$ is a methyl group and $R^5$ and $R^6$ are the same and have the meaning of hydrogen.

Step 4:

Each of the 3'-N-demethyl derivatives of oleandomycin from Step 3 is subjected to reductive N-methylation in 3' position with 1–6.2 equivalents of formaldehyde (36%) in the presence of 1–4.2 equivalents of formic acid (98–100%) or some other hydrogen source, in a solvent inert in the reaction such as halogenated hydrocarbons, lower alcohols or lower ketones, preferably chloroform, at the reflux temperature of the reaction mixture, to obtain, respectively, in case of 3A, a compound 4A of the general formula (I), wherein $R^1$–$R^4$ have the meanings as given for the compound 2A, $R^5$ is hydrogen and $R^6$ is a methyl group, and in case of 3B, a compound 4B of the general formula (I), wherein $R^1$–$R^4$ have the meanings as given for the compound 2B, $R^5$ is hydrogen and $R^6$ is a methyl group, and in case of 3C, a compound 4C of the general formula (I), wherein $R^1$–$R^4$ have the meanings as given for the compound 3C, $R^5$ is hydrogen and $R^6$ is a methyl group.

Fragments of the formulas (II), (III) and (V) are shown without space orientation of the bonds and define all combinations of orientation of bonds in order to comprise all possible stereoconfigurations, i.e. epimers.

Pharmaceutically acceptable addition salts which are also an object of the present invention, are obtained by reacting novel oleandomycin derivatives of the general formula (I) with an at least equimolar amount of a corresponding inorganic or organic acid such as hydrochloric, hydroiodic, sulfuric, phosphoric, acetic, propionic, trifluoroacetic, maleic, citric, stearic, succinic, ethylsuccinic, methanesulfonic, benzenesulfonic, p-toluenesulfonic, laurylsulfonic acids etc., in a solvent inert in the reaction. Addition salts are isolated by filtration if insoluble in the solvent inert in the reaction, by precipitation by means of non-solvents or evaporation of solvents, most often by a lyophilization process.

The process for preparing novel derivatives of oleandomycin is illustrated by the following non-limiting Examples.

EXAMPLE 1

2'-O,3'-N-bis(Benzyloxycarbonyl)-3'-N-demethyl-oleandomycin

To a solution of oleandomycin (50.98 g, 0.0741 mol) in benzene (385 ml) NaHCO$_3$ was added (226.74 g; 2.6990 mol) and the reaction mixture was heated under stirring to the reflux temperature (55–60° C.). 95% benzyloxycarbonylchloride (312 ml; 354.20 g; 2.0762 mol) was added drop by drop for 4 hours under stirring. The reaction mixture was stirred for further 24 hours at the same temperature and left for 42 hours at room temperature. After the filtration the precipitate was washed with benzene (75 ml) and the benzene solution was extracted three times with 100 ml of 0.25 N HCl and once with 100 ml water. The benzene solution was dried over CaCl$_2$, filtered and evaporated under reduced pressure to give a viscous oily residue (306.4 g), which was purified by low pressure chromatography on a column of silica gel 60 (230–400 mesh ASTM). To this effect the crude oily product was applied to a silica gel column (500 g) under a nitrogen pressure of 0.5. $10^5$ Pa. The excess of the reagent was removed by passing CH$_2$Cl$_2$ (1400 ml) and then there was obtained 2'-O,3'-N-bis(benzyloxycarbonyl)-3'-N-demethyl-oleandomycin (19.77 g) using the system methylene chloridemethanol 95:5 (1000 ml) and evaporation of fractions containing the chromatographically homogenous title product with the following physico-chemical constants:

EI-MS m/z 943
TLC, methylene chloride-methanol, 95:5   Rf0.397
     toluene-ethyl acetate, 1:1           Rf0.420

(IR) (KBr) cm$^{-1}$ 3480, 2980, 2940, 1755, 1710, 1460, 1385, 1325, 1295, 1255, 1115, 1060, 1005, 990, 760, 700. $^1$H NMR (300 MHz, CDCl$_3$) δ 7.35–7.28 (Ph), 5.11, 5.09 (CH$_2$—Ph), 5.58 (H-13), 4.95 (H-1"), 4.66 (H-2'), 4.49 (H-1'), 4.41 (H-3'), 3.80 (H-11), 3.70 (H-5"), 3.46 (H-3") 3.40 (3"-OCH$_3$), 3.40 (H-5), 3.15 (H-4"), 3.00 (H-10), 3.00 (H-8a), 2.85 (H-8b), 2.83 (H-2), 2.80 (3'-NHCH$_3$), 2.35 (H-2"a), 2.24 (H-7a), 1.73 (H-7b), 1.69 (H-6), 1.69 (H-4'a), 1.65 (H-4), 1.62 (H-12), 1.53 (H-2"b), 1.31 (5"-CH$_3$), 1.26 (13-CH$_3$), 1.22 (5'-CH$_3$), 1.20 (2-CH$_3$), 1.03 (6-CH$_3$), 1.03 (10-CH$_3$), 0.89 (4-CH$_3$), 0.86 (12-CH$_3$), $^{13}$C NMR (75 MHz, CDCl$_3$) δ 214.2 (C-9), 176.4 (C-1), 156.4, 156.0 (OCO), 154.4, 154.3 (NCO), 136.6 (O Ph), 134.9 (NPh), 128.5–127.6 (Ph), 101.8 (C-1'), 99.0 (C-1"), 86.1 (C-5), 80.1 (C-3), 77.6 (C-3"), 75.8 (C-4"), 74.6 (C-2'), 70.2 (C-13), 69.2 (C-5'), 68.7 (C-11), 68.5 (C-5"), 69.6, 69.5, 67.1, 66.9 (CH$_2$—Ph), 61.9 (C-8), 56.2 (3"-OCH$_3$), 54.7 (C-3'), 50.2 (8-CH$_2$), 44.5 (C-10), 44.3 (C-2), 42.2 (C-4), 41.4 (C-12), 35.4 (C-4'), 33.8 (C-6), 33.6 (C-2"), 30.0 (C-7), 28.9 (3'-NHCH$_3$), 20.4 (5'-CH$_3$), 18.1 (13-CH$_3$), 17.6 (5"-CH$_3$), 9.0 (4-CH$_3$), 8.5 (12-CH$_3$), 6.4 (10-CH$_3$).

EXAMPLE 2

Method A

2'-O,3'-N-bis(benzyloxycarbonyl)-3'-N-demethyl-11,12,13-trisnor-1-methoxy-10,11-seco-oleandomycin (2A)

2'-O,3'-N-bis(benzyloxycarbonyl)-3'-N-demethyl-epi-oleandomycin (2B) 2'-O,3'-N-bis(benzyloxycarbonyl)-3'-N-demethyl-1-methoxy-10,11-anhydro-1,13-seco-oleandomycin (2C)

To a solution of 2'-O,3'-N-bis(benzyloxycarbonyl)-3'-N-demethyl-oleandomycin (6.00 g, 6.4 mmol) from Example 1 in a dimethylsulfoxide-tetrahydrofaran mixture (1:1, 48 ml) cooled to 0–5° C., methyl iodide (1.32 ml; 20.7 mmol) diluted with a dimethylsulfoxide-tetrahydrofaran mixture (1:1, 12 ml) and 60% sodium hydride in mineral oil (0.76 g; 17.5 mmol) were added step by step for 1 hour. The reaction mixture was stirred for farther 2 hours at the same temperature. The reaction was interrupted by addition of triethyl amine (10 ml), it was stirred for 10 minutes, a saturated NaCl solution (80 ml) was added, it was stirred for farther 10 minutes and the inorganic part was filtered off. The filtrate was extracted with ethyl acetate (80 ml), the organic layer was washed two more times with a saturated NaCl solution (80 ml) and dried over $K_2CO_3$. After filtration and evaporation under reduced pressure a yellowish amorphous precipitate (5.36 g) was obtained. By chromatography on a silica gel column using a system toluene-ethyl acetate=1:1, from the reaction mixture (2.82 g) a chromatographically homogenous compound 2A (0.40 g), a chromatographically homogenous compound 2B (0.12 g), and a chromatographically homogenous compound 2C (0.39 g), characterized by the following physico-chemical constants, were isolated.

| 2A | | |
|---|---|---|
| TLC, | methylene chloride-methanol, 95:5 | Rf0.587 |
| | toluene-ethyl acetate, 1:1 | Rf0.687 |

(IR) (KBr) $cm^{-1}$ 3480, 2980, 2940, 1750, 1710, 1455, 1385, 1335, 1295, 1260, 1165, 1110, 1055, 1005, 830, 790, 760, 700. $^1$H NMR (300 MHz, $CDCl_3$) δ 7.35–7.27 (Ph), 5.12, 5.09 ($CH_2$—Ph), 4.89 (H-1"), 4.64 (H-2'), 4.49 (H-1'), 4.46 (H-3'), 3.90 (H-3), 3.70 (1-$OCH_3$), 3.70 (H-5"), 3.61 (H-5'), 3.45 (H-3"), 3.41 (H-5), 3.40 (3"-$OCH_3$), 3.12 (H-4"), 2.85 (3'-$NHCH_3$), 2.79 (H-2), 2.76 (H-8a), 2.74 (H-8b), 2.56 (H-7a), 2.39 (H-10a), 2.34 (H-10b), 2.27 (H-2"a), 1.90 (H-6), 1.73 (H-4), 1.70 (H-4'a), 1.61 (H-4'b), 1.46 (H-2"b), 1.22 (5'-$CH_3$), 1.21 (5"-$CH_3$), 1.18 (2-$CH_3$), 1.16 (H-7b), 1.03 (6-$CH_3$), 1.03 (10-$CH_3$), 0.90 (4-$CH_3$). $^{13}$C NMR (75 MHz, $CDCl_3$) δ 209.5 (C-9), 175.2 (C-1), 156.1, 155.7 (OCO), 154.2, 154.1 (NCO), 136.3 (O Ph), 1349 (N Ph), 129.2–127.3 (Ph), 100.9 (C-1'), 97.8 (C-1"), 82.9 (C-5), 79.7 (C-3), 77.8 (C-3"), 75.5 (C-4"), 74.3 (C-2'), 68.2 (C-5'), 68.2 (C-5"), 69.3, 69.1, 67.1, 66.9 ($CH_2$—Ph), 62.1 (C-8), 56.1 (3"-$OCH_3$), 54.5 (C-3'), 51.5 (1-$OCH_3$), 49.9 (8-$CH_2$), 42.0 (C-2), 39.4 (C-4), 35.9 (C-4'), 33.9 (C-2"), 32.4 (C-6), 31.7 (C-7), 29.1 (10-$CH_2$), 28.4 (3'-$NHCH_3$), 20.3 (5'-$CH_3$), 17.6 (6-$CH_3$), 17.4 (5"-$CH_3$), 11.9 (2-$CH_3$), 9.7 (4-$CH_3$), 7.1 (10-$CH_3$).

| 2B | | |
|---|---|---|
| TLC, | methylene chloride-methanol, 95:5 | Rf0.447 |
| | toluene-ethyl acetate, 1:1 | Rf0.520 |

(IR) (KBr) $cm^{-1}$ 3480, 2970, 2930, 1750, 1725, 1700, 1450, 1380, 1330, 1295, 1255, 1160, 1110, 1060, 990, 785, 755, 695, 665. $^1$H NMR (300 MHz, $CDCl_3$) δ 7.38–7.27 (Ph), 5.13, 5.08 ($CH_2$—Ph), 4.88 (H-13), 4.88 (H-1 "), 4.66 (H-2'), 4.47 (H-3'), 4.41 (H-1'), 3.85 (H-11), 3.68 (H-5"), 3.66 (H-3), 3.62 (H-5'), 3.43 (H-3"), 3.40 (3"-$OCH_3$), 3.33 (H-5), 3.26 (H-10), 3.13 H-4"), 2.83 (H-8a), 2.83 (H-8b), 2.81 (3'-$NHCH_3$), 2.67 (H-2), 2.64 (H-7a), 2.34 (H-2"a), 1.76 (H-6), 1.72 (H-12), 1.70 (H-4'a), 1.70 (H-4), 1.62 (H-4'b), 1.50 (H-2"b), 1.32 (H-7b), 1.28 (13-$CH_3$), 1.27 (5"-$CH_3$), 1.22 (5-$CH_3$), 1.18 (2-$CH_3$), 1.12 (6-$CH_3$) 1.06 (10-$CH_3$), 1.03 (12-$CH_3$), 0.96 (4-$CH_3$). $^{13}$C NMR (75 MHz, $CDCl_3$) δ 211.3 (C-9), 174.9 (C-1), 156.5, 156.1 (OCO), 154.5, 154.4 (NCO), 136.6 (O Ph), 135.0 (NPh), 128.5–127.6 (Ph), 101.6 (C-1'), 98.8 (C-1"), 83.9 (C-5), 79.8 (C-3), 77.7 (C-3"), 75.8 (C-4"), 74.6 (C-2'), 73.2 (C-13), 70.1 (C-11), 68.5 (C-5"), 68.3 (C-5'), 69.6, 69,4, 67,0, 66.9 ($CH_2$—Ph), 61.5 (C-8), 56.2 (3"-$OCH_3$ 54.6 (C-3'), 51.2 (8-$CH_2$), 44.6 (C-2), 43.3 (C-4), 42.4 (C-10), 40.5 (C-12), 35.5 (C-4'), 33.7 (C-2"), 32.0 (C-6), 30.7 (C-7), 28.5 (3'-$NHCH_3$), 20.4 (5'-$CH_3$), 17.5 (5"-$CH_3$), 15.2 (13-$CH_3$), 13.6 (2-$CH_3$), 10.5 (12-$CH_3$), 10.2 (10-$CH_3$), 9.2 (4-$CH_3$).

| 2C | | |
|---|---|---|
| TLC, | methylene chloride-methanol, 95:5 | Rf0.420 |
| | toluene-ethyl acetate, 1:1 | Rf0.360 |

(IR) (KBr) $cm^{-1}$ 3460, 2970, 2930, 1740, 1690, 1450, 1380, 1330, 1290, 1250, 1160, 1110, 1050, 1000, 785, 755, 695, 665. $^1$H NMR (300 MHz, $CDCl_3$) δ 7.34–7.20 (Ph), 6.74 (H-11), 5.10, 5.09 ($CH_2$—Ph), 4.84 (H-1"), 4.64 (H-2'), 4.51 (H-1'), 4.43 (H-3'), 3.94 (H-3), 3.84 (H-13), 3.72 (H-5"), 3.58 (H-5') 3.44 (1-$OCH_3$), 3.42 (H-3"), 3.38 (3 -$OCH_3$), 3.29 (H-5), 3.09 (H-4"), 2.85 (3'-$NHCH_3$), 2.83 (H-8a), 2.83 (H-7a), 2.75 (H-8b), 2.73 (H-12), 2.65 (H-2), 2.19 (H-2"a), 1.84 (10-$CH_3$), 1.78 (H-4), 1.74 (H-4'a), 1.69 (H-6), 1.39 (H-2"b), 1.24 (5"-$CH_3$), 1.22 (H-7b), 1.22 (13-$CH_3$), 1.22 (5"-$CH_3$), 1.08 (12-$CH_3$), 1.07 (2-$CH_3$), 1.00 (6-$CH_3$), 0.82 (4-$CH_3$). $^{13}$C NMR (75 MHz, $CDCl_3$) δ 199.0 (C-9), 175.7 (C-1), 156.3, 156.0 (OCO), 154.6, 154.4 (NCO), 147.7 (C-11), 136.5 (O Ph), 135.2 (N Ph), 134.1 (C-10), 128.7–127.4 (Ph), 101.0 (C-1'), 97.4 (C-1"), 82.6 (C-5), 79.6 (C-3), 78.0 (C-3"), 75.8 (C-4"), 74.3 (C-2'), 70.3 (C-13), 68.6 (C-5'), 68.3 (C-5"), 69.6, 69.3, 67.1, 66.9 ($CH_2$—Ph), 62.0 (C-8), 56.1 (3"-$OCH_3$), 55.1 (C-3'), 51.7 (1-$OCH_3$), 50.0 (8-$CH_2$), 41.0 (C-12), 40.3 (C-2), 38.6 (C-4), 37.0 (C-7), 35.4 (C-4'), 33.9 (C-2"), 33.1 (C-6), 28.9 (3'$NHCH_3$), 20.9 (5'-$CH_3$), 20.7 (13-$CH_3$), 17.5 (5"-$CH_3$), 16.8 (6-$CH_3$), 14.0 (2-$CH_3$), 11.5 (10-$CH_3$), 10.1 (12-$CH_3$), 9.4 (4-$CH_3$).

EXAMPLE 2

Method B

2'O,3'-N-bis(Benzyloxycarbonyl)-3'-N-demethyl-11,12,13-trisnor-1-methoxy-10,11-seco-oleandomycin (2A)

2'-O,3'-N-bis(Benzyloxycarbonyl)-3'-N-demethyl-1-methoxy-10,11-anhydro-1,13-seco-oleandomycin (2C)

To a solution of 2'-O,3'-N-bis(benzyloxycarbonyl)-3'-N-demethyl-oleandomycin (6.00 g, 6.4 mmol) from Example 1 in a dimethylsulfoxide-tetrahydrofuran mixture (1:1, 12 ml) cooled to 0–5° C., methyl iodide (1.32 ml, 20.7 mmol) diluted with a dimethyl-sulfoxide-tetrahydrofuran mixture (1:1, 12 ml) and 60% sodium. hydride in mineral oil (1.04 g; 23.9 mmol) were added step by step for 1 hour. The reaction mixture was stirred for further 2 hours at the same temperature. The reaction was interrupted by addition of triethyl amine (10 ml), it was stirred for 10 minutes, a saturated NaCl solution (80 ml) was added, it was stirred for further 10 minutes and the inorganic part was filtered off The filtrate was extracted with ethyl acetate (80 ml), the organic layer was washed two more times with a saturated NaCl solution (80 ml) and dried over $K_2CO_3$. After filtration and evaporation under reduced pressure, a yellowish amorphous precipitate (5.90 g) was obtained. By chromatography on a silica gel column using the system toluene-ethyl acetate= 1:1, from the reaction mixture (2.95 g) a chromatographically homogenous compound 2A (0.12 g) and a chromatographically homogenous compound 2C (0.40 g), characterized by the physicochemical constants as given in Example 2, Method A, were isolated.

EXAMPLE 2

Method C

2'-0,3'-N-bis(Benzyloxycarbonyl)-3'-N-demethyl-11, 12,13-trisnor-1-methoxy-10,11-seco-oleandomycin (2A)

2'-0,3'-N-bis(Benzyloxycarbonyl)-3'-N-demethyl-epi-oleandomycin (2B)

To a solution of 2'-O,3'-N-bis(benzyloxycarbonyl)-3'-N-demethyl-oleandomycin (6.00 g, 6.4 mmol) from Example 1 in a dimethylsulfoxide-tetrahydrofuran mixture (1:1, 48 ml) cooled to 0–5° C., methyl iodide (0.52 ml; 8.1 mmol) diluted with a dimethylsulfoxide-tetrahydrofuran mixture (1:1, 12 ml) and 60% sodium hydride in mineral oil (0.30 g; 6.8 mmol) were added step by step for 1 hour. The reaction mixture was stirred for further 2 hours at the same temperature. The reaction was interrupted by addition of triethyl amine (10 ml), it was stirred for 10 minutes, a saturated NaCl solution (80 ml) was added, it was stirred for further 10 minutes and the inorganic part was filtered off. The filtrate was extracted with ethyl acetate (80 ml), the organic layer was washed two more times with a saturated NaCl solution (80 ml) and dried over $K_2CO_3$. After filtration and evaporation under reduced pressure, a yellowish amorphous precipitate (5.59 g) was obtained. By chromatography on a silica gel column using the system toluene-ethyl acetate= 1:1, from the reaction mixture (2.80 g) a chromatographically homogenous compound 2A (0.44 g) and a chromatographically homogenous compound 2B (0.66 g), characterized by the physico-chemical constants as given in Example 2, Method A, were isolated.

EXAMPLE 3

3'-N-demethyl-11,12,13-trisnor-1-methoxy-10,11-seco-oleandomycin (3A)

The product 2A (2.65 g, 3 mmol) was dissolved in ethanol (42 ml), the pH was adjusted to 6.8 with a buffer pH 5 (0.19 ml HOAc, 0.30 g NaOAc and 10 ml water), Pd/C 10% (0.28 g) was added and the reaction mixture was hydrogenated under stirring for 3.5 hours in an autoclave at a hydrogen pressure of $10^5$ Pa at room temperature. The catalyst was filtered off, the filtrate was evaporated to a viscous syrup, $CHCl_3$ (50 ml) and water (50 ml) were added, the pH of the mixture was adjusted with 20% NaOH to 9.0, the layers were separated and the aqueous extract was extracted three more times with $CHCl_3$ (50 ml). Combined organic extracts were dried over $K_2CO_3$, filtered, evaporated under reduced pressure, optionally purified by chromatography on a silica gel column using the system chloroform-methanol-conc. ammonia 60:10:1 to give the title product (1.45 g) with the following physicochemical constants:

EI-MS m/z 604
TLC, chloroform-methanol-conc. ammonia, 60:10:1 Rf0.602
methylene chloride-methanol-conc. ammonia, 90:9:1.5 Rf0.358

(IR) (KBr) $cm^{-1}$ 3310, 2970, 2930, 1730, 1715, 1465, 1455, 1380, 1260, 1195, 1155, 1070, 1045, 1005, 985, 900, 755, 665. $^1H$ NMR (300 MHz, $CDCl_3$) δ 4.90 (H-1"), 4.27 (H-1'), 3.99 (H-3), 3.74 (H-5"), 3.70 (1-$OCH_3$), 3.55 (H-5'), 3.46 (H-5), 3.42 (H-3"), 3.40 (3"-$OCH_3$), 3.19 (H-2'), 3.17 (H-4"), 2.81 (H-2), 2.77 (H-8a), 2.74 (H-8b), 2.67 (H-7a), 2.52 (H-3'), 2.41 (H-10a), 2.40 (3'-$NHCH_3$), 2.35 (H-10b), 2.29 (H-2"a), 2.05 (H-6), 1.93 (H-4'a), 1.87 (H-4), 1.49 (H-2"b), 1.28 (5"-$CH_3$), 1.21 (2-$CH_3$), 1.20 (H-4'b), 1.20 (5-$CH_3$), 1.10 (H-7b), 1.04 (4-$CH_3$), 1.02 (6-$CH_3$), 1.02 (10-$CH_3$). $^{13}C$ NMR (75 MHz, $CDCl_3$) δ 209.9 (C-9), 175.7 (C-1), 103.3 (C-1'), 98.1 (C-1"), 82.3 (C-5), 80.2 (C-3), 77.8 (C-3"), 75.4 (C-4"), 73.4 (C-2'), 68.5 (C-5'), 68.4 (C-5"), 62.1 (C-8), 59.9 (C-3'), 56.2 (3"-$OCH_3$), 51.4 (1-$OCH_3$), 49.8 (8-$CH_2$), 42.0 (C-2), 39.1 (C-4), 36.6 (C-4'), 33.9 (C-2"), 32.7 (3'-$NHCH_3$), 32.6 (C-7), 32.3 (C-6), 29.0 (10-$CH_2$), 20.6 (5'-$CH_3$), 17.2 (5"-$CH_3$), 17.0 (6-$CH_3$), 11.7 (2-$CH_3$), 10.3 (4-$CH_3$), 6.9 (10-$CH_3$).

EXAMPLE 4

3'-N-Demethyl-epi-oleandomycin (3B)

The product 2B (1.42 g, 1.5 mmol) was dissolved in ethanol (23 ml), the pH was adjusted to 6.8 with a buffer pH 5 (0.19 ml HOAc, 0.30 g NaOAc and 10 ml water), Pd/C 10% (0.15 g) was added and the reaction mixture was hydrogenated under stirring for 4.5 hours in an autoclave at a hydrogen pressure of $10^5$ Pa at room temperature. The isolation was carried out as in Example 3. After evaporation under reduced pressure, the product was optionally purified by chromatography on a silica gel column using the system chloroform-methanol-conc. ammonia 60:10:1 to give the title product (0.99 g) with the following physico-chemical constants:

EI-MS m/z 674
TLC, chloroform-methanol-conc. ammonia, 60:10:1 Rf0.370
methylene chloride-methanol-conc. ammonia, 90:9:1.5 Rf0.170

(IR) (KBr) $cm^{-1}$ 3450, 2980, 2940, 2900, 1730, 1715, 1465, 1455, 1385, 1255, 1190, 1155, 1070, 1050, 1000, 875, 755, 670. $^1H$ NMR (300 MHz, $CDCl_3$) δ 5.09 (H-13), 4.90 (H-1"), 4.19 (H-1'), 3.74 (H-11), 3.72 (H-5"), 3.71 (H-3), 3.54 (H-5'), 3.44 (H-5), 3.44 (H-3"), 3.41 (3"-$OCH_3$), 3.23 (H-10), 3.17 (H-2'), 3.15 (H-4"), 2.88 (H-8a), 2.88 (H-8b), 2.77 (H-2), 2.53 (H-3'), 2.41 (3'-$NHCH_3$), 2.34 (H-2"a), 2.21 (H-7a), 1.95 (H-4'a), 1.94 (H-6), 1.85 (H-7b), 1.70 (H-4), 1.53 (H-12), 1.51 (H-2"b), 1.30 (5"-$CH_3$), 1.27 (13-$CH_3$), 1.21 (5-$CH_3$), 1.20 (2-$CH_3$), 1.18 (H-4'b), 1.13 (6-$CH_3$), 1.10 (12-$CH_3$), 1.09 (10-$CH_3$), 1.09 (4-$CH_3$). $^{13}C$ NMR (75 MHz, $CDCl_3$) δ 212.2 (C-9), 174.5 (C-1), 102.9 (C-1'), 99.9 (C-1"), 81.5 (C-3), 81.1 (C-5), 77.7 (C-3"), 75.6 (C-4"), 73.9 (C-2'), 71.1 (C-13), 70.0 (C-11), 68.6 (C-5"), 68.5 (C-5'), 61.2 (C-8), 59.6 (C-3'), 56.3 (3"-$OCH_3$), 49.9 (8-$CH_2$), 44.6 (C-2), 42.6 (C-12), 41.8 (C-10), 40.5 (C-4), 36.9 (C-4'), 33.9 (C-2"), 32.9 (3-$NHCH_3$), 31.7 (C-7), 30.6 (C-6), 20.7 (5'-$CH_3$), 20.2 (6-$CH_3$), 17.6 (5"-$CH_3$), 16.7 (13-$CH_3$), 14.8 (2-$CH_3$), 10.1 (12-$CH_3$), 9.9 (4-$CH_3$), 9.2 (10-$CH_3$).

EXAMPLE 5

3'-N-Demethyl-1-methoxy-1,13-seco-oleandomycin-9,13-hemiketal (3C)

The product 2C (1.28 g, 1.3 mmol) was dissolved in ethanol (21 ml), the pH was adjusted to 6.8 with a buffer pH 5 (0.19 ml HOAc, 0.30 g NaOAc and 10 ml water), Pd/C 10% (0.18 g) was added and the reaction mixture was hydrogenated under stirring for 6 hours in an autoclave at a hydrogen pressure of $10^5$ Pa at room temperature. The isolation was carried out as in Example 3. After evaporation under reduced pressure, the product was optionally purified by chromatography on a silica gel column using the system chloroform-methanol-conc. ammonia 60:10:1 to give the title product (0.81 g) with the following physico-chemical constants:

EI-MS m/z 690
TLC chloroform-methanol-conc. ammonia, 60:10:1 Rf0.556
methylene chloride-methanol-conc. ammonia, 90:9:1.5 Rf0.302

(IR) (KBr) cm$^{-1}$ 3470, 2980, 2940, 2900, 1735, 1465, 1455, 1385, 1265, 1205, 1160, 1075, 1040, 1000, 900, 760, 670. $^1$H NMR (300 MHz, CDCl$_3$) δ 4.84 (H-1"), 4.30 (H-1'), 4.15 (H-13), 4.03 (H-3), 3.76 (H-5"), 3.71 (1-OCH$_3$), 3.56 (H-5'), 3.45 (H-3"), 3.42 (H-5), 3.39 (3-OCH$_3$), 3.18 (H-2'), 3.14 (H-4"), 2.84 (H-8a), 2.79 (H-2), 2.63 (H-8b), 2.54 (H-3'), 2.44 (H-7a), 2.41 (3'-NHCH$_3$), 2.26 (H-2"a), 2.10 (H-10), 1.96 (H-6), 1.94 (H-4'a), 1.92 (H-4), 1.85 (H-4), 1.85 (H-11a), 1.66 (H-12), 1.47 (H-2"b), 1.40 (H-11b), 1.36 (H-7b), 1.28 (5"-CH$_3$), 1.22 (5'-CH$_3$), 1.19 (H-4'b), 1.16 (2-CH$_3$), 1.04 (6-CH$_3$), 1.00 (13-CH$_3$), 0.98 (12-CH$_3$), 0.98 (4-CH$_3$), 0.81 (10-CH$_3$). $^{13}$C NMR (75 MHz, CDCl$_3$) δ 175.8 (C-1), 103.7 (C-1'), 98.1 (C-1"), 97.4 (C-9), 82.7 (C-5), 80.6 (C-3), 78.0 (C-3"), 75.6 (C-4"), 74.0 (C-2'), 68.7 (C-5'), 68.5 (C-5"), 66.9 (C-13), 60.5 (C-8), 60.1 (C-3'), 56.2 (3"-OCH$_3$), 51.7 (1-OCH$_3$), 49.5 (8-CH$_2$), 41.7 (C-2), 38.5 (C-4), 36.9 (C-4'), 35.5 (C-11), 34.0 (C-2"), 32.9 (3'-NHCH$_3$), 32.0 (C-12), 31.7 (C-6), 30.8 (C-7), 27.4 (C-10), 20.9 (5'-CH$_3$), 18.3 (4-CH$_3$), 18.0 (13-CH$_3$), 17.4 (5"-CH$_3$), 15.9 (10-CH$_3$), 11.6 (12-CH$_3$), 11.0 (2-CH$_3$), 10.5 (6-CH$_3$).

EXAMPLE 6

11,12,13-trisnor-1-methoxy-10,11-seco-oleandomycin (4A)

To a solution of 3'-N-demethyl-11,12,13-trisnor-1-methoxy-10,11-seco-oleandomycin from Example 3 (0.90 g; 1.5 mmol) in CHCl$_3$ (60 ml), 36% formaldehyde (0.236 ml, 8.5 mmol) and 98–100% formic acid (0.217 ml; 5.8 mmol) were added. The reaction mixture was stirred for 3.5 hours under reflux, cooled to room temperature, poured into water (60 ml), the pH of the mixture was adjusted with 2N NaOH to 9.0, the layers were separated and the aqueous layer was extracted three more times with CHCl$_3$ (30 ml). Combined organic extracts were dried over K$_2$CO$_3$, filtered, evaporated under reduced pressure, optionally purified on a silica gel column using the system chloroform-methanol-conc. ammonia 60:10:1 to give the title product (0.97 g) with the following physico-chemical constants:

EI-MS m/z 618
TLC, chloroform-methanol-conc. ammonia, 60:10:1 Rf0.787
methylene chloride-methanol-conc. ammonia, 90:9:1.5 Rf0.575

(IR) (KBr) cm$^{-1}$ 3450, 2970, 2930, 1735, 1715, 1460, 1455, 1380, 1260, 1195, 1160, 1075, 1045, 1000, 795, 755. $^1$H NMR (300 MHz, CDCl$_3$) δ 4.92 (H-1"), 4.27 (H-1'), 4.00 (H-3), 3.77 (H-5"), 3.69 (1-OCH$_3$), 3.48 (H-5'), 3.46 (H-3"), 3.41 (H-5), 3.40 (3"-OCH$_3$), 3.23 (H-2'), 3.14 (H-4"), 2.83 (H-2), 2.78 (H-8a), 2.75 (H-8b), 2.66 (H-7a), 2.49 (H-3'), 2.43 (H-10a), 2.28 (3'-N(CH$_3$)$_2$), 2.37 (H-10b), 2.31 (H-2"a), 2.04 (H-6), 1.88 (H-4), 1.65 (H-4'a), 1.48 (H-2"b), 1.29 (5"-CH$_3$), 1.24 (H-4'b), 1.23 (2-CH$_3$), 1.20 (5-CH$_3$), 1.20 (H-7b), 1.12 (4-CH$_3$), 1.05 (6-CH$_3$), 1.03 (10-CH$_3$). $^{13}$C NMR (75 MHz, CDCl$_3$) δ 209.9 (C-9), 175.6 (C-1), 104.0 (C-1'), 98.5 (C-1"), 83.1 (C-5), 80.5 (C-3), 77.9 (C-3"), 75.7 (C-4"), 70.1 (C-2'), 68.9 (C-5'), 68.2 (C-3'), 62.1 (C-8), 56.0 (3"-OCH$_3$), 51.4 (1-OCH$_3$), 49.9 (8-CH$_2$), 42.6 (C-2), 40.0 (3'-N(CH$_3$)$_2$), 39.6 (C-4), 33.9 (C-2"), 31.9 (C-6), 31.8 (C-7), 29.0 (10-CH$_2$), 28.4 (C-4'), 20.8 (5'-CH$_3$), 17.5 (6-CH$_3$), 17.2 (5"-CH$_3$), 12.7 (2-CH$_3$), 10.1 (4-CH$_3$), 7.0 (10-CH$_3$).

EXAMPLE 7 epi-Oleandomycin (4B)

To a solution of 3'-N-demethyl-epi-oleandomycin from Example 4 (1.12 g; 1.7 mmol) in CHCl$_3$ (75 ml), 36% formaldehyde (0.291 ml; 10.5 mmol) and 98–100% formic acid (0.267 ml, 7.1 mmol) were added. The reaction mixture was stirred for 7 hours under reflux. The isolation was carried out as in Example 6. After evaporation under reduced pressure, the product was optionally purified on a silica gel column using the system methylene chloride-methanol-conc. ammonia 90:9:1.5 to give the title product (1.11 g) with the following physico-chemical constants:

EI-MS m/z 688
TLC, chloroform-methanol-conc. ammonia, 60:10:1 Rf0.667
methylene chloride-methanol-conc. ammonia, 90:9:1.5 Rf0.415

(IR) (KBr) cm$^{-1}$ 3457, 2974, 2937, 2788, 1717, 1456, 1382, 1331, 1258, 1185, 1163, 1109, 1078, 1050, 1005, 934, 871, 831, 755, 666. $^1$H NMR (600 MHz, CDCl$_3$) δ 4.96 (H-13), 4.88 (H-1"), 4.21 (H-1'), 3.83 (H-11), 3.74 (H-5"), 3.72 (H-3), 3.48 (H-5'), 3.46 (H-3"), 3.41 (3"-OCH$_3$), 3.41 (H-5), 3.26 (H-10), 3.26 (H-2'), 3.15 (H-4"), 2.79 (H-8a), 2.79 (H-8b), 2.78 (H-2), 2.63 (H-7a), 2.55 (H-3'), 2.36 (H-2"a), 2.33 (3'-N(CH$_3$)$_2$), 1.88 (H-6), 1.84 (H-4), 1.77 (H-12), 1.71 (H-4'a), 1.53 (H-7b), 1.51 (H-2"b), 1.29 (5"-CH$_3$), 1.29 (13-CH$_3$), 1.27 (H-4'b), 1.23 (2-CH$_3$), 1.22 (5'-CH$_3$), 1.17 (4-CH$_3$), 1.15 (6-CH$_3$), 1.07 (12-CH$_3$), 1.06 (10-CH$_3$). $^{13}$C NMR (600 MHz, CDCl$_3$) δ 210.6 (C-9), 174.1 (C-1), 104.0 (C-1'), 99.8 (C-1"), 83.0 (C-5), 81.9 (C-3), 77.7 (C-3"), 75.7 (C-4"), 72.8 (C-13), 70.1 (C-2'), 69.4 (C-11), 68.9 (C-5'), 68.4 (C-5"), 65.1 (C-3'), 60.9 (C-8), 56.1 (3"-OCH$_3$), 51.1 (8-CH$_2$), 44.8 (C-2), 42.4 (C-10), 42.3 (C-4), 40.1 (C-12), 39.9 (3'-N(CH$_3$)$_2$), 33.9 (C-2"), 31.7 (C-7), 31.0 (C-6), 28.3 (C-4'), 20.8 (5'-CH$_3$), 19.2 (6-CH$_3$), 17.2 (5"-CH$_3$), 15.5 (13-CH$_3$), 14.5 (2-CH$_3$), 11.0 (12-CH$_3$), 9.6 (4-CH$_3$), 8.7 (10-CH$_3$).

EXAMPLE 8

1-methoxy-1,13-seco-oleandomycin-9,13-hemiketal (4C)

To a solution of 3'-N-demethyl-1-methoxy-1,13-seco-oleandomycin-9,13-hemiketal (1.19 g; 1.7 mmol) from Example 5 in CHCl$_3$, (80 ml), 36% formaldehyde (0.274 ml; 9.9 mmol) and 98–100% formic acid (0.252 ml; 6.7 mmol) were added. The reaction mixture was stirred for 5 hours under reflux. The isolation was carried out as in Example 6. After evaporation under reduced pressure the product was optionally purified on a silica gel column using the system methylene chloride-methanol-conc. ammonia 90:9:1.5 to give the title product (0.85 g) with the following physico-chemical constants:

| | |
|---|---|
| EI-MS m/z 704 | |
| TLC, chloroform-methanol-conc. ammonia, 60:10:1 | Rf0.759 |
| methylene chloride-methanol-conc. ammonia, 90:9:1.5 | Rf0.509 |

(IR) (KBr) cm$^{-1}$ 3465, 2973, 2936, 2788, 1733, 1456, 1383, 1298, 1260, 1199, 1163, 1109, 1078, 1050, 1005, 987, 932, 895, 833, 755, 666. $^1$H NMR (500 MHz, CDCl$_3$) δ 4,88 (H-1"), 4.29 (H-1'), 4.15 (H-13), 4.00 (H-3), 3.78 (H-5"), 3,69 (1-OCH$_3$), 3.49 (H-5'), 3.45 (H-3"), 3.41 (H-5), 3.40 (3"-OCH$_3$), 3.27 (H-2'), 3.14 (H-4"), 2.83 (H-8a), 2.81 (H-2), 2.67 (H-8b), 2.52 (H-3'), 2.38 (H-7a), 2.30 (3'-N (CH$_3$)$_2$, 2.25 (H-2"), 2.12 (H-10), 1.87 (H-6), 1.85 (H-4), 1.82 (H-11a), 1.67 (H-4'a), 1.62 (H-12), 1.47 (H-7b), 1.44 (H-2"b), 1.37 (H-11b), 1.28 (H-4'b), 1.28 (5"-CH$_3$), 1.23 (5'-CH$_3$), 1.16 (2-CH$_3$), 1.11 (6-CH$_3$), 1.04 (4-CH$_3$), 1.04 (13-CH$_3$), 0.99 (12-CH$_3$), 0.81 (10-CH$_3$). $^{13}$C NMR (500 MHz, CDCl$_3$) δ 175.7 (C-1), 104.2 (C-1'), 98.1 (C-1"), 97.4 (C-9), 83.0 (C-5), 80.6 (C-3), 78.0 (C-3"), 75.8 (C-4"), 70.3 (C-2'), 69.0 (C-5'), 68.3 (C-5"), 66.9 (C-13), 65.2 (C-3'), 60.5 (C-8), 56.1 (3"-OCH$_3$), 51.6 (1-OCH$_3$), 49.6 (8-CH$_2$), 42.0 (C-2), 40.1 (3'-N(CH$_3$)$_2$), 38.9 (C-4), 35.6 (C-11), 34.0 (C-2"), 32.1 (C-12), 31.3 (C-6), 30.0 (C-7), 28.8 (C-4'), 27.3 (C-10), 21.0 (5'-CH$_3$), 18.3 (4-CH$_3$), 18.2 (13-CH$_3$), 17.4 (5"-CH$_3$), 15.9 (10-CH$_3$), 11.7 (12-CH$_3$), 11.5 (2-CH$_3$) 10.2 (6-CH$_3$).

What is claimed is:

1. A compound of formula (I) and pharmaceutically acceptable addition salts thereof with inorganic or organic acids,

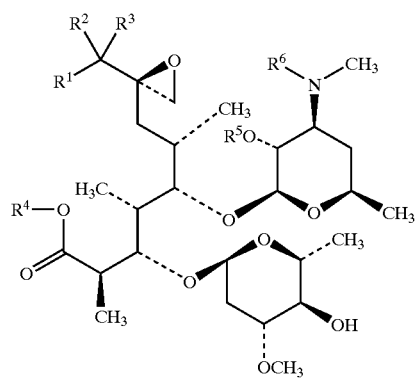

wherein

R$^1$ has the individual meaning of —CH$_2$CH$_3$ group, of a fragment of the formula (II), together with R$^2$ has the meaning of a fragment of the formula (III) or together with R$^4$ has the meaning of a fragment of the formula (V), wherein said Fragment of formula V is selected from the group consisting of V2, V3, V4, V5, V6, V7, V8, V9, V10, V11, V12, V13, V14, V15, and V16;

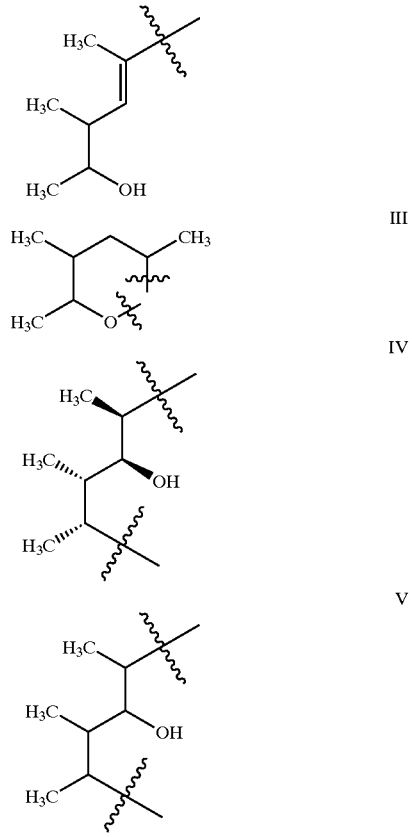

R$^2$ together with R$^3$ has the meaning of a ketone or together with R$^1$ has the meaning of a fragment of the formula (III);

R$^3$ has the individual meaning of OH group or together with R$^2$ has the meaning of a ketone; R$^4$ has the individual meaning of a methyl group, or together with R$^1$ has the meaning of a fragment of the formula (V), wherein said Fragment of formula V is selected from the group consisting of V2, V3, V4, V5, V6, V7, V8, V9, V10, V11, V12, V13, V14, V15, and V16;

R$^5$ has the individual meaning of hydrogen or a benzyloxycarbonyl group;

R$^6$ has the individual meaning of hydrogen, a methyl group or a benzyloxycarbonyl group.

2. A compound according to claim 1, characterized in that R$^1$ together with R$^4$ has the meaning of a fragment of the formula (IV), R$^2$ together with R$^3$ has the meaning of a ketone and R$^5$ and R$^6$ are the same and have the meaning of a benzyloxycarbonyl group.

3. A compound according to claim 1, characterized in that R$^1$ has the meaning of —CH$_2$CH$_3$ group, R$^2$ together with R$^3$ has the meaning of a ketone, R$^4$ is a methyl group and R$^5$ and R$^6$ are the same and have the meaning of a benzyloxycarbonyl group.

4. A compound according to claim 1, characterized in that R$^1$ together with R$^4$ has the meaning of a fragment of the formula (V), R$^2$ together with R$^3$ has the meaning of a ketone and R$^5$ and R$^6$ are the same and have the meaning of a benzyloxycarbonyl group.

5. A compound according to claim 1, characterized in that R$^1$ has the meaning of a fragment of the formula (II), R$^2$ together with R$^3$ has the meaning of a ketone, R$^4$ is a methyl group and R⁵ and R⁶ are the same and have the meaning of a benzyloxycarbonyl group.

6. A compound according to claim 1, characterized in that R¹ has the meaning of —CH₂CH₃ group, R² together with R³ has the meaning of a ketone, R⁴ is a methyl group and R⁵ and R⁶ are the same and have the meaning of hydrogen.

7. A compound according to claim 1, characterized in that R¹ together with R⁴ has the meaning of a fragment of the formula (V), R² together with R³ has the meaning of a ketone and R⁵ and R⁶ are the same and have the meaning of hydrogen.

8. A compound according to claim 1, characterized in that R¹ together with R² has the meaning of a fragment of the formula (III), R³ is an OH group, R⁴ is a methyl group and R⁵ and R⁶ are the same and have the meaning of hydrogen.

9. A compound according to claim 1, characterized in that R¹ has the meaning of —CH₂CH₃ group, R² together with R³ has the meaning of a ketone, R⁴ and R⁶ are the same and have the meaning of a methyl group and R⁵ is hydrogen.

10. A compound according to claim 1, characterized in that R¹ together with R⁴ has the meaning of a fragment of the formula (V), R² together with R³ has the meaning of a ketone, R⁵ is hydrogen and R⁶ is a methyl group.

11. A compound according to claim 1, characterized in that R¹ together with R² has the meaning of a fragment of the formula (III), R³ is an OH group, R⁴ and R⁶ are the same and have the meaning of a methyl group and R⁵ is hydrogen.

12. A process for preparing a compound of formula (I)

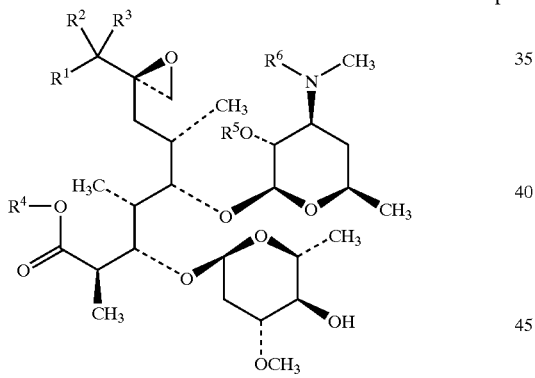

I wherein

R¹ has the individual meaning of —CH₂CH₃ group, of a fragment of the formula (II), together with R² has the meaning of a fragment of the formula (III) or together with R⁴ has the meaning of a fragment of the formula (IV) or a fragment of the formula (V),

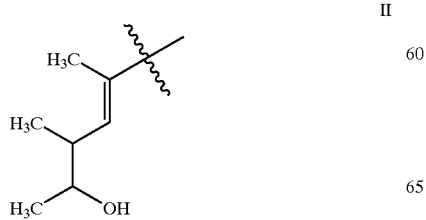

II

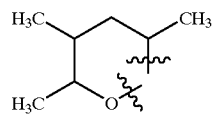

III

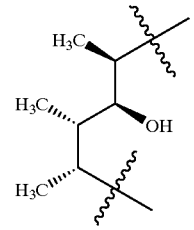

IV

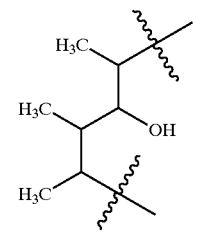

V

R² together with R³ has the meaning of a ketone or together with R¹ has the meaning of a fragment of the formula (III), R³ has the individual meaning of OH group or together with R² has the meaning of a ketone, R⁴ has the individual meaning of a methyl group, or together with R¹ has the meaning of a fragment of the formula (IV) or of a fragment of the formula (V), R⁵ has the individual meaning of hydrogen or a benzyloxycarbonyl group, R⁶ has the individual meaning of hydrogen, a methyl group or a benzyloxycarbonyl group, and pharmaceutically acceptable addition salts thereof with inorganic or organic acids, the method comprising the steps of:

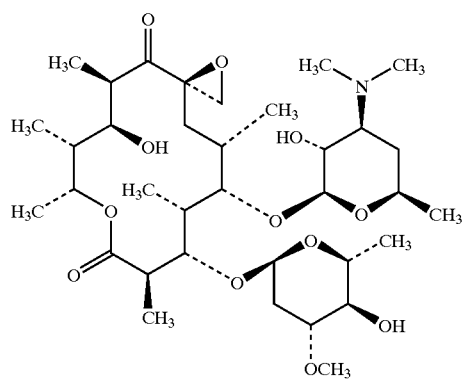

VI a) reacting oleandomycin of the formula (VI) with benzyloxycarbonyl chloride in the presence of a first base, in a first inert solvent to obtain a 2'-O,3'-N-bis(benzyloxycarbonyl)-N-demethyloleandomycin of formula (I), wherein R¹ together with R⁴ has the meaning of a fragment of the formula (IV), R² together with R³ has the meaning of a ketone and R⁵ and R⁶ are the same and have the meaning of a benzyloxycarbony l group, b) methylating said 2'-O,3'-N-bis(benzyloxycarbonyl)-N-demethyloleandomycin with a methylating agent in the presence of a corresponding second base, at a temperature from −15° C. to room temperature, in an appropriate aprotic solvent or solvent mixture, to yield a mixture comprising a plurality of compounds having formula (I), c) separating said mixture on a silica gel column in the system toluene-ethyl acetate=1:1 to obtain a first chromatographically homogenous compound 2A, wherein $R^1$ has the meaning of —$CH_2CH_3$ group, $R^2$ together with $R^3$ has the meaning of a ketone, $R^4$ is a methyl group and $R^5$ and $R^6$ are the same and have the meaning of a benzyloxycarbonyl group, a second chromatographically homogenous compound 2B of formula (I), wherein $R^1$ together with $R^4$ has the meaning of a fragment of the formula (V), $R^2$ together with $R^3$ has the meaning of a ketone and $R^5$ and $R^6$ are the same and have the meaning of a benzyloxycarbonyl group, and a third chromatographically homogenous compound 2C of formula (I), wherein $R^1$ has the meaning of a fragment of the formula (II), $R^2$ together with $R^3$ has the meaning of a ketone, $R^4$ is a methyl group and $R^5$ and $R^6$ are the same and have the meaning of a benzyloxycarbonyl group, d) reacting each said compound 2A, 2B, and 2C, separately, under hydrogenolysis conditions in a lower alcohol solution, in the presence of NaOAc/HOAc buffer (pH 5) with a catalyst, under hydrogen pressure of $10^5$ Pa at room temperature to obtain, respectively, in case of 2A, a compound 3A of the general formula (I), wherein $R^1$–$R^4$ have the meaning as given for the compound 2A and $R^5$ and $R^6$ are the same and have the meaning of hydrogen, and in case of 2B, a compound 3B of the general formula (I), wherein $R^1$–$R^4$ have the meaning as given for the compound 2B and $R^5$ and $R^6$ are the same and have the meaning of hydrogen, and in case of 2C, a compound 3C of the general formula (I), wherein $R^1$ together with $R^2$ has the meaning of a fragment of the formula (III), $R^3$ is an OH group, $R^4$ is a methyl group and $R^5$ and $R^6$ are the same and have the meaning of hydrogen, e) reductively methylating separately each of said compounds 3A, 3B, and 3C in the 3' position with 1–6.2 equivalents of formaldehyde (36%) in the presence of 1–4.2 equivalents of a hydrogen source in a second inert solvent, at the reflux temperature of the reaction mixture, to obtain, respectively, in case of 3A, a compound 4A of the general formula (I), wherein $R^1$–$R^4$ have the meanings as given for the compound 2A, $R^5$ is hydrogen and $R^6$ is a methyl group, and in case of 3B, a compound 4B of the general formula (I), wherein $R^1$–$R^4$ have the meanings as given for the compound 2B, $R^5$ is hydrogen and $R^6$ is a methyl group, and in case of 3C, a compound 4C of the general formula (I), wherein $R^1$–$R^4$ have the meanings as given for the compound 3C, $R^5$ is hydrogen and $R^6$ is a methyl group, f) optionally reacting said compounds 4A, 4B, and 4C with inorganic or organic acids to obtain pharmaceutically acceptable addition salts thereof.

13. A process for preparing a compound of formula (I) according to claim 12, wherein said first base in sodium hydrogen carbonate.

14. A process for preparing a compound of formula (I) according to claim 12, wherein said first inert solvent is selected from the group consisting of benzene and toluene.

15. A process for preparing a compound of formula (I) according to claim 12, wherein said methylating agent is methyl iodide.

16. A process for preparing a compound of formula (I) according to claim 12, wherein said second base is sodium hydride.

17. A process for preparing a compound of formula (I) according to claim 12, wherein said methylation is performed at from 0–5° C.

18. A process for preparing a compound of formula (I) according to claim 12, wherein said aprotic solvent is a 1/1 mixture of DMSO and THF.

19. A process for preparing a compound of formula (I) according to claim 12, wherein said lower alcohol is ethanol.

20. A process for preparing a compound of formula (I) according to claim 12, wherein said catalyst is selected from the group consisting of palladium black and palladium on carbon.

21. A process for preparing a compound of formula (I) according to claim 12, wherein said hydrogen source is formic acid (98–100%).

22. A process for preparing a compound of formula (I) according to claim 12, wherein said second inert solvent is selected from the group consisting of halogenated hydrocarbons, lower alcohols, and lower ketones.

23. A compound of formula (I) and pharmaceutically acceptable addition salts thereof with inorganic or organic acids, wherein $R^1$ together with $R^4$ has the meaning of a fragment of formula IV and $R^2$ together with $R^3$ has the meaning of a ketone, wherein:

$R^5$ means a benzyloxycarbonyl group and $R^6$ means a group selected from a hydrogen, a methyl group, and a benzyloxycarbonyl group.

24. A compound of formula (I) and pharmaceutically acceptable addition salts thereof with inorganic or organic acids, wherein $R^1$ together with $R^4$ has the meaning of a fragment of formula IV and $R^2$ together with $R^3$ has the meaning of a ketone, wherein:

$R^5$ means a hydrogen and $R^6$ means a group selected from a hydrogen and a benzyloxycarbonyl group.

\* \* \* \* \*